United States Patent [19]

McAlear et al.

[11] 4,103,073
[45] Jul. 25, 1978

[54] MICROSUBSTRATES AND METHOD FOR MAKING MICROPATTERN DEVICES

[75] Inventors: James H. McAlear, Gaithersburg; John M. Wehrung, Potomac, both of Md.

[73] Assignee: Dios, Inc., Potomac, Md.

[21] Appl. No.: 647,872

[22] Filed: Jan. 9, 1976

[51] Int. Cl.² .................... B05D 5/12; B32B 9/02
[52] U.S. Cl. .................................. 428/474; 96/35.1; 96/36.2; 427/43; 427/54; 427/44; 427/98; 427/123; 427/229; 427/259; 427/264; 427/270; 427/271; 427/272; 427/282; 427/287; 427/338; 427/340; 427/407 R; 427/407 A; 427/414; 427/419 D; 428/459

[58] Field of Search ............... 96/36.2, 35.1; 427/43, 427/44, 98, 123, 271, 229, 93, 259, 264, 270, 272, 273, 277, 282, 287, 338, 340, 358, 54, 385 R, 385 A, 407 R, 407 A, 414, 404, 419 D; 428/411, 474, 459

[56] References Cited

U.S. PATENT DOCUMENTS

| 3,575,733 | 4/1971 | Cecil | 427/43 |
| 3,885,060 | 5/1975 | Hirai et al. | 427/43 |
| 3,914,462 | 10/1975 | Morishita et al. | 427/43 |

*Primary Examiner*—Cameron K. Weiffenbach
*Attorney, Agent, or Firm*—Roylance, Abrams, Berdo & Kaul

[57] ABSTRACT

Micropattern devices, such as electronic microcircuits, are produced by establishing on a substrate base a film of resist material, such as a polymeric film, containing dispersed therethrough a substantial proportion of an enzyme and then producing a pattern of a metal by reactions depending upon presence of the enzyme.

17 Claims, No Drawings

MICROSUBSTRATES AND METHOD FOR MAKING MICROPATTERN DEVICES

BACKGROUND OF THE INVENTION

Expanding usage of electronic microcircuits has resulted in a rapid advance in the art of producing articles in the nature of a metallic micropattern material. Recently developed procedures employ, e.g., a substrate base of silicon covered with an insulating layer of silicon dioxide, and an electron resist covering the silicon dioxide layer, the resist being selectively irradiated with an electron beam in accordance with the micropatterning step to be performed, the irradiated resist being removed to expose the selected area or areas of the silicon dioxide, and metal then being deposited on the exposed area or areas by thin film techniques.

Though such procedures have achieved considerable success, there has been a continuing need not only for decreasing the time required for, e.g., electron beam irradiation but also for an alternative to the depositing steps involved in conventional thin film formation and for an improvement in edge definition of the metallic micropattern.

OBJECTS OF THE INVENTION

A general object of the invention is to provide a method for producing metallic micropatterns without dependence upon, e.g., vacuum deposition of the metal.

Another object is to devise such a method by which the desired micropattern can be written in a variety of ways and, when written with an electron beam, provides a marked reduction in the writing time.

A further object is to provide such a method which can achieve micropatterns of superior edge definition.

SUMMARY OF THE INVENTION

According to method embodiments of the invention, a film of a suitable resist, typically of a polymeric material capable of being depolymerized when subjected to radiant energy such as that of an electron beam, is established on the substrate base, with the film of resist material having dispersed therethrough a substantial proportion of an enzyme selected from the group consisting of the transferases and the oxidoreductases (oxyreductases). The micropattern is then written in such fashion that the enzyme is left in active form in the areas which are to receive metal or other functional material, and the functional material is provided by chemical reaction dependent upon the activity of the specific enzyme employed. Article embodiments of the invention are microsubstrates comprising a substrate base and a film of resist material supported by the base and containing, dispersed uniformly therethrough, a substantial proportion of an enzyme.

GENERAL DESCRIPTION OF THE INVENTION

The invention is based upon the observation that enzymes which will catalyze a reaction yielding a product from which an elemental metal or other functional material can be obtained in situ are compatable with film-forming materials suitable for use in microsubstrates. Enzymes suitable for use according to the invention are the transferases which are effective to catalyze the transfer of an inorganic radical containing the desired metal from a source compound to a compound from which the metal can be derived in elemental form, and the oxidases.

The film forming materials most suitable for use as a carrier for the enzyme or enzymes are those polymeric materials which can be polymerized in situ on the substrate base under conditions which will not inactivate the enzyme. Typical of such materials are the vinyl monomers, especially the methacrylates, including, for example, methyl methacrylate, ethyl methacrylate and butyl methacrylate, capable of polymerization to the solid state at low temperature under the influence of ultra violet radiation.

Microsubstrates are prepared according to the invention by agitating the enzyme, in dry (lyophilized) form, in the liquid monomer or monomers at low temperature, so as to obtain a dispersion of the enzyme in the monomeric material, with the enzyme essentially in molecular solution. The resulting dispersion is spread evenly on the face of the substrate base and polymerized, with or without a polymerization initiation, under the influence of ultra violet radiation under controlled temperature conditions such that the temperature does not exceed the highest temperature at which the enzyme remains active. For production of electronic microcircuits, the substrate base can be a silicon wafer covered by an insulating film of silicon dioxide. The enzyme-containing resist film can be 0.1–5 microns thick and can be established, e.g., by centrifugal spreading.

The amount of enzyme provided in the resist film should be tailored to the particular chemical reactions to be carried out with the aid of the enzyme and, ordinarily, should be at least 1% based on the weight of the film former used to produce the resist film. In most cases, higher proportions of the enzyme are advantageous and it is advantageous to introduce as much of the enzyme as can be uniformly distributed in the monomers. Amounts of the enzyme equal to as much as 50% of the total weight of the resist film are achievable.

Such microsubstrates can be further processed in a number of ways to produce a desired micropattern of metal or other functional material. Thus, the film can be removed mechanically, as by use of a stylus, in those areas which are to constitute the negative, so that the enzyme-containing film remains only in the positive areas, where the functional material is to be established. The entire surface of the substrate can then be treated with an aqueous solution of both a compound from which, e.g., metal-containing radicals are liberated by the enzyme and a compound which will react with the liberated radicals to yield a product from which the metal can be derived in elemental form. Employing phosphatase as the enzyme, the aqueous treating solution can be of creatinine phosphate and lead nitrate, with the enzyme liberating phosphate radicals and with the lead nitrate reacting to form lead phosphate. The lead phosphate can be thermally reduced to deposit metallic lead in the positive area of the pattern, residual polymeric material being destroyed by the heat employed for the thermal reduction, so that the metallic lead deposits directly on the substrate base.

Though mechanical steps, matter beam etching, and irradiation with electromagnetic radiation are all useful ways tracing to establish the desired micropattern, it is particularly advantageous to write the pattern with a focussed electron beam. Electron beam writing can be employed in either of two modes, one using the beam at a dosage level adequate to depolymerize the polymeric material, so that the irradiated portions can be selectively removed by dissolution with the corresponding monomer, the other using the beam at a higher dosage level adequate to deactivate the enzyme in the irradiated areas, in which case treatment with the aqueous solution can proceed without requiring removal of any of the polymeric material. In this connection, it will be understood that conventionally established films of polymeric resist material are previous to aqueous solutions, and that an enzyme, such as phosphatase, supported in a 0.1-5 micron thick film of, e.g., polymethyl methacrylate will react with constituents of a solution in which the film is immersed.

Irradiation of the enzyme-containing resist film with a focussed electron beam at a dosage in the range of from $10^{-7}$ $10^{-5}$ coulombs per square centimeter at 10,000 EV is effective to depolymerize most polymeric resist film formers, without deactivating the enzyme. Irradiation with a focussed electron beam at a dosage level of from a $10^{-7}$ to 25 coulombs per square centimeter at 10,000 EV is adequate both to totally depolymerize the polymeric material and totally deactivate the enzyme in the irradiated area. Depending upon the micropattern to be formed, the electron beam can have a diameter of from about 50 to about 500 Angstrom units.

While the invention is particularly useful when practiced to produce micropatterns of conductive metal, it can be employed to provide micropatterns of other functional materials. Thus, for example, a micropattern of osmium black can be established for use as a mask against electron beam irradiation.

The following example illustrates the manner in which a microsubstrate can be prepared according to the invention.

EXAMPLE 1

Ninety parts by volume of butyl methacrylate and 10 parts by volume of methyl methacrylate are blended and the blend purged of oxygen by bubbling nitrogen gas through the liquid monomers. The liquid blend is cooled to $-10°$ C. over dry ice and acetone, an amount of benzoyl peroxide equal to 1% of the combined weight of the two monomers is added, and the liquid thoroughly mixed. A known volume of commercially available lyophilized phosphatase is placed in an Ehrlenmeyer flask and an equal volume of the monomer blend is added, followed by ultrasonic agitation for 30 mins. to thoroughly disperse the enzyme through the monomer blend. The resulting material constitites a uniform molecular dispersion of phosphatase in the liquid monomers. A silicon wafer having a silicon dioxide surface is mounted in horizontal position, silicon dioxide face up, for rotation about a vertical axis. The phosphatase-containing monomer blend is then supplied by an eye dropper to the center of the upper face of the dish while the dish is rotated to spread a thin film of the liquid uniformly over the face of the wafer. The wafer is then placed face up under a nitrogen-filled glass container and subjected to ultra violet light from a conventional laboratory "black light" overnight with the ultra violet source 6 in. from the wafer and the temperature of the wafer maintained below 40° C. The amount of liquid supplied and the speed and time of centrifugal spreading are controlled to provide a film which, after polymerization is complete, is approximately 1 micron thick. The finished film can be characterized as a solid matrix of copolymerized polybutyl methacrylate and polymethyl methacrylate through which the macromolecules of phosphatase are evenly distributed, with the phosphatase retaining its enzymatic activity.

The following examples illustrate the use of such microsubstrates in accordance with the invention.

EXAMPLE 2

A microsubstrate prepared according to Example 1 is employed to produced a supported micropattern of conductive lead, as in an electronic microcircuit. The microsubstrate is placed in a computer-controlled electron microscope and a negative of the desired micropattern is traced on the phosphatase-containing polymeric film of the microsubstrate with the electron beam of the microscope focussed to a diameter of approximately 100 Angstrom units and with an irradiation dosage of $10^{-6}$ coulomb per square centimeter at 10,000 EV. As a result, the polymeric material in the ares traced by the beam is depolymerized. Monomeric methyl methacrylate is then flowed over the surface of the microsubstrate for 10 minutes to dissolve away the depolymerized polymeric material and the enzyme contained thereby, leaving the silicon dioxide layer of the substrate base exposed throughout the negative area. The microsubstrate is then washed with distilled deionized water and then immersed in an aqueous solution of creatinine phosphate and lead nitrate for 3 hours at room temperature, the active phosphatase retained by the polymeric material remaining on the positive areas of the micropattern causing the creatinine phosphate to break down into creatinine and phosphate radicals, with the phosphate radicals reacting with lead nitrate to yield lead phosphate. The microsubstrate is then again washed with distilled deionized water. The cleaned microsubstrate is then placed in an oven and maintained for 5 hours at 320° C. under a non-oxidizing atmosphere to reduce the lead phosphate to elemental lead and to destroy the polymeric material remaining in the positive area. The elemental lead so produced is deposited on the silicon dioxide film as a conductive body extending throughout the positive area of the micropattern, the negative area being constituted by exposed portions of the silicon dioxide film.

EXAMPLE 3

A microsubstrate produced according to Example 1 is placed in an electron microscope and the negative area of the desired micropattern is traced with the beam dosage at $10^{-1}$ coulomb per square centimeter at 10,000 EV, with the result that the polymeric material in the negative area is depolymerized and the phosphatase contained thereby is completely deactivated. The microsubstrate is then immersed for 3 hrs. in an aqueous solution containing both creatinine phosphate and lead nitrate, the active phosphatase remaining in the positive area of the micropattern causing the creatinine phosphate to break down into creatinine and phosphate radicals, only in the positive area, and the lead nitrate reacting there with the liberated phosphate radicals to produce lead phosphate. The resulting product is then baked in an oven for 5 hours at 320° C. under non-oxidizing conditions to reduce the lead phosphate to metallic lead in the positive areas and to destroy all of the polymeric material. The finished product is essentially the same as obtained in Example 2.

EXAMPLE 4

A microsubstrate is prepared as in Example 1, but with peroxidase substituted for phosphatase, and the resulting microsubstrate employed to produce a micropattern effective as a mask against electron beam irradiation. The electron beam of a computer-controlled electron microscope is employed to trace on the peroxidase-containing polymeric film of the microsubstrate a negative of the micropattern desired for the mask, using a dosage of $10^{-1}$ coulomb per square centimeter at 10,000 EV. The irradiated material in this negative area, including both the depolymerized polymeric material and the deactivated peroxidase contained thereby, is removed by flowing methyl methacrylate monomer over the microsubstrate for 10 mins. The microsubstrate is then washed thoroughly with distilled deionized water. An aqueous solution of hydrogen peroxide and diazobenzidine tetrahydrazide is then flowed over the microsubstrate for 10 minutes and the substrate then thoroughly washed with distilled deionized water. A 1% weight solution of osmium tetraoxide in distilled deionized water is then prepared and that solution flowed over the microsubstrate for 10 mins., resulting in a copious deposit of osmium black in the portion of the polymeric film now constituting the positive of the desired micropattern. The resulting product is a micropattern represented by the deposited osmium black, carried by the residual polymeric material which is in turn supported by the silicon dioxide-covered silicon wafer as a substrate base.

What is claimed is:

1. A microsubstrate comprising
a support presenting a supporting surface; and
a thin film overlying said supporting surface and adhered thereto;
   said film comprising at least one active enzyme selected from the group consisting of transferases and oxidoreductases,
   said enzyme being present in the form of macromolecules uniformly distributed throughout the film.

2. The method for forming a micropattern, comprising
establishing a solid film containing at least one enzyme selected from the group consisting of the transferases and the oxidoreductases,
   said at least one enzyme being present in the form of macromolecules retaining their enzymatic activity and which are uniformly distributed throughout said film;
treating said film to restrict said at least one enzyme in its active state to the predetermined areas of said film which are defined by the desired micropattern; and
treating said predetermined areas of said film to carry out throughout said predetermined areas at least one chemical reaction which depends upon presence of said at least one enzyme in active state and which produces a particular reaction product operatively suitable for the purpose of the desired micropattern.

3. In the fabrication of articles exhibiting a micropattern of a particular material carried by a surface of a support, the method comprising
establishing on the surface of the support a solid film containing at least one enzyme selected from the group consisting of the transferases and the oxidoreductases,
   said at least one enzyme being present in the form of macromolecules retaining their enzymatic activity and which are uniformly distributed throughout said solid film;
treating said solid film to restrict said at least one enzyme in its active state to predetermined areas defined by the desired micropattern; and
treating said predetermined areas of said solid film to carry out at least one chemical reaction which is dependent upon presence of said at least one enzyme in its active state and which produces said particular material, whereby said particular material is established on the surface of the support throughout said predetermined areas.

4. The method according to claim 3, wherein said at least one enzyme is peroxidase; and
said step of treating said predetermined areas of said film comprises
   first treating said predetermined areas of said film with a solution of hydrogen peroxide and diazobenzidine tetrahydrazide, and
   then treating said predetermined areas of said film with a solution of osmium tetroxide,
   whereby osmium black is deposited in said predetermined areas of said film.

5. The method according to claim 3, wherein
said solid film is of polymeric material; and
said enzyme is present in an amount equal to 1–50% of the weight of the polymeric material of said film.

6. The method according to claim 3, wherein
said at least one enzyme is phosphatase; and
said step of treating said predetermined areas of said solid film comprises immersing said film in an aqueous solution containing creatinine phosphate and lead nitrate, whereby lead phosphate is liberated on the areas occupied by phosphatase.

7. The method according to claim 6, wherein
said film is of at least one vinyl polymer; and
the method further comprises
baking the support and said film to reduce the lead phosphate to metallic lead and destroy the polymeric film.

8. The method according to claim 3, wherein
the particular material resulting from said at least one chemical reaction is metallic.

9. The method according to claim 8, wherein said particular material is a metal in elemental form.

10. The method according to claim 3, wherein
said film is of polymeric material; and
said step of treating said solid film is carried out by irradiating said film with a focussed electron beam.

11. The method according to claim 10, wherein
said step of irradiating said film is carried out by irradiating those areas of said film which constitute the negative of the desired micropattern at an electron beam dosage level adequate to depolymerize the polymeric material of said film;
the method further comprising
dissolving the depolymerized portion of said film and removing the dissolved material from the support before carrying out said step of treating said predetermined areas of said film to carry out said at least one chemical reaction.

12. The method according to claim 10, wherein
said step of irradiating said film is carried out by irradiating those areas of said film which constitute the negative of the desired micropattern at an electron beam dosage level adequate to deactivate said at least one enzyme.

13. The method according to claim 12, further comprising dissolving the polymeric material in the irradiated areas of said film and removing the dissolved polymeric material and the deactivated enzyme from the support in those areas before carrying out said step of treating said predetermined areas of said film to carry out said at least one chemical reaction.

14. The method according to claim 12, wherein said step of treating said predetermined areas to carry out at least one chemical reaction is carried out while the irradiated portions of said film, within which said at least one enzyme is deactivated, remain in place.

15. The method according to claim 12, wherein said film is of at least one vinyl polymer and has a thickness of 0.1–5 microns.

16. The method according to claim 15, wherein said at least one enzyme is phosphatase.

17. The method according to claim 15, wherein said at least one enzyme is peroxidase.

\* \* \* \* \*